United States Patent [19]

Wong

[11] Patent Number: 5,053,754
[45] Date of Patent: Oct. 1, 1991

[54] SIMPLE FIRE DETECTOR

[75] Inventor: Jacob Y. Wong, Santa Barbara, Calif.

[73] Assignee: Gaztech Corporation, Goleta, Calif.

[21] Appl. No.: 503,214

[22] Filed: Apr. 2, 1990

[51] Int. Cl.$^5$ .................................................. G08B 17/10
[52] U.S. Cl. .................................. 340/632; 73/24.02;
73/31.07; 250/343
[58] Field of Search ...................... 340/627, 628, 632;
250/573, 343, 381; 73/23.31, 24.02, 31.01, 31.07

[56] References Cited

U.S. PATENT DOCUMENTS

| 4,288,790 | 9/1981 | Schnell | 340/628 |
| 4,738,266 | 4/1988 | Thatcher | 128/664 X |
| 4,928,687 | 5/1990 | Lampotang et al. | 128/205.23 X |

Primary Examiner—Donnie L. Crosland
Assistant Examiner—Jeffery A. Hofsass
Attorney, Agent, or Firm—Daniel C. McKown

[57] ABSTRACT

A fire detector that responds more rapidly than the widely used smoke detectors senses increases in the concentration of carbon dioxide associated with a fire. The build-up of carbon dioxide is sensed by measuring the concomittant increase in the absorption of a beam of radiation whose wavelength is located at a strong absorption band of carbon dioxide. The device is considerably simplified by the use of a window to the sample chamber that is highly permeable to carbon dioxide but which keeps out particles of dust, smoke, oil, and water. This permits the fire detector to be built of very inexpensive materials.

24 Claims, 3 Drawing Sheets

Fig. 5

SIMPLE FIRE DETECTOR

BACKGROUND OF THE INVENTION

1. Field of the Invention

The present invention is in the field of early warning devices for fire detection and more particularly relates to a compact apparatus which has no moving parts and which measures the concentration and the rate of change in the concentration of carbon dioxide at the onset of a fire as a means for early and rapid detection of the fire.

2. Related Patent Applications

A first companion patent application by the present inventor, titled "Rapid Fire Detector" was filed simultaneously with the present application. As will be discussed more fully below, the invention of the first companion application uses a dual wavelength technique, while the present invention uses a single wavelength technique.

A second companion patent application by the present inventor, titled "Gas Sample Chamber" was also filed simultaneously with the present application. Although the present invention employs the sample chamber of the second companion patent application, the patent-ability of the present invention rests on an independent basis.

The Prior Art

The fire detectors that are available commercially today fall into three basic classifications, namely flame sensing, thermal and smoke detectors. This classification is designed to respond to the three principal types of energy and matter characteristics of a fire environment: flame, heat and smoke.

The flame sensing detector is designed to respond to the optical radiant energy generated by the diffusion flame combustion process—the illumination intensity and the frequency of flame modulation. Two types of flame detectors are commonly in use: the ultraviolet (UV) detectors which operate beyond the visible at wavelengths below 4,000 A, and the infrared detectors which operate in the wavelengths above 7,000 A. To prevent false signals from the many sources of ultraviolet and infrared optical radiation present in most hazard areas, the detectors are programmed to respond only to radiation with frequency modulation within the flicker frequency range for flame (5–30 Hz).

Flame detectors generally work well and seldom generate false alarms. However, they are relatively complex and expensive fire detectors which are not amenable to low-cost and mass-oriented usage. Instead they are mostly utilized in specialized high-value and unique protection areas such as aircraft flight simulators, aircraft hangars, nuclear reactor control rooms, etc.

Thermal detectors are designed to operate from thermal energy output - the heat - of a fire. This heat is dissipated throughout the area by laminar and turbulent convection flow. The latter is induced and regulated by the fire plume thermal column effect of rising heated air and gases above the fire surface. There are two basic types of thermal detectors: the fixed temperature type and the rate-of-rise detector type. The fixed temperature type further divides into the spot type and the line type. The spot detector involves a relatively small fixed unit with a heat-responsive element contained within the unit or spot location of the detector. With the line detector the thermal reactive element is located along a line consisting of thermal-sensitive wiring or tubing. Line detectors can cover a greater portion of the hazard area than can spot detectors.

Fixed temperature thermal fire detectors rate high on reliability, stability and maintainability but low on sensitivity. In modern buildings with high air flow ventilation and air conditioning systems, placing the fixed temperature detector is a difficult engineering problem. Consequently, this type of thermal fire detector is not widely used outside of very specialized applications.

A rate-of-rise detector type thermal fire detector is usually installed where a relatively fast-burning fire is expected. The detector operates when the fire plume raises the air temperature within a chamber at a rate above a certain threshold of operation—usually 15° F. per minute. However, if a fire develops very slowly and the rate of temperature rise never exceeds the detector's threshold for operation, the detector may not sense the fire.

The newest type of thermal fire detector is called a rate-compensated detector which is sensitive to the rate of temperature rise as well as to a fixed temperature level which is designed into the detector's temperature rating. Even with this dual approach, the most critical problem for effective operation of thermal fire detectors is the proper placement of detectors relative to the hazard area and the occupancy environment. Consequently, this type of fire detector is seldom found in everyday households.

By far the most popular fire detector in use in everyday life today is the smoke detector. Smoke detectors respond to the visible and invisible products of combustion. Visible products of combustion consist primarily of unconsumed carbon and carbon-rich particles; invisible products of combustion consist of solid particles smaller than approximately five (5) microns, various gases, and ions. All smoke detectors can be classified into two basic types: photoelectric type which responds to visible products of combustion and ionization type which responds to both visible and invisible products of combustion.

The photoelectric type is further divided into 1) projected beam and 2) reflected beam. The projected beam type of smoke detectors generally consist of a series of sampling piping from the holds or other protected space on the ship to the photoelectric detector. The air sample is drawn into the piping system by an electric exhaust pump. The photoelectric detector is usually enclosed in a metal tube with the light source mounted at one end and the photoelectric cell at the other end. This type of detector is rather effective due to the length of the light beam. When visible smoke is drawn into the tube, the light intensity of the beam received in the photoelectric cell is reduced because it is obscured by the smoke particles. The reduced level of light intensity causes an unbalanced condition in the electrical circuit to the photocell which activates the alarm. The projected beam or smoke obscuration detector is one of the most established types of smoke detectors. In addition to use on ships, these detectors are commonly used to protect high-value compartments or other storage areas, and to provide smoke detection for plenum areas and air ducts.

The reflected light beam smoke detector has the advantage of a very short light beam length, making it adaptable to incorporation in the spot type smoke detector. The projected beam smoke detector discussed earlier becomes more sensitive as the length of the light beam increases, and often a light beam of 5 or 10 feet long is required. However, the reflected light beam type of photoelectric smoke detector is designed to operate with a light beam only 2 or 3 inches in length. A reflected beam visible light smoke detector consists of a light source, a photoelectric cell mounted at right angles to the light source, and a light catcher mounted opposite to the light source.

Ionization type smoke detectors detect both the visible and invisible particle matter generated by the diffusion flame combustion. As indicated previously, visible particulate matter ranges from 4 to 5 microns in size, although smaller particles can be seen as a haze when present in a high mass density. The ionization detector operates most effectively on particles from 1.0 to 0.01 microns in size. There are two basic types of ionization detectors. The first type has a bipolar ionized sampling chamber which is the area formed between two electrodes. A radioactive alpha particle source is also located in this area. The oxygen and nitrogen molecules of air in the chamber are ionized by alpha particles from the radioactive source. The ionized pairs move towards the electrodes of the opposite signs when electrical voltage is applied, and a minute electrical current flow is established across the sampling chamber. When combustion particles enter the chamber they attach themselves to the ions. Since the combustion particles have a greater mass, the mobility of the ions now decreases, leading to a reduction of electrical current flow across the sampling chamber. This reduction in electrical current flow initiates the detector alarm.

The second type of ionization smoke detector has a unipolar ionized sampling chamber instead of a bipolar one. The only difference between the two types is the location of the area inside the sampling chamber that is exposed to the alpha source. In the case of the bipolar type the entire chamber is exposed leading to both positive and negative ions (hence the name bipolar). In the case of the unipolar type only the immediate area adjacent the positive electrode (anode) is exposed to the alpha source. This results in only one predominant type of ions (negative ions) in the electrical current flow between the electrodes (hence the name unipolar).

Although unipolar and bipolar sampling chambers use different principles of detector design they both operate by the combustion products creating a reduced current flow and thus activating the detector. In general the unipolar design is superior in giving the ionization smoke detectors a greater level of sensitivity and stability, with fewer fluctuations of current flow to cause false signals from variations in temperature, pressure and humidity. Most ionization smoke detectors available commercially today are of the unipolar type.

For the past two decades the ionization smoke detectors have dominated the fire detector market. One of the reasons is that the other two classes of fire detectors, namely the flame sensing detectors and the thermal detectors are appreciably more complex and costlier than the ionization smoke detectors. They are therefore mainly used only in specialized high-value and unique protection areas. In recent years, because of their relatively high cost, even the photoelectric smoke detectors have fallen behind significantly in sales to the ionization type. The ionization types are generally less expensive, easier to use and can operate for a full year with just one 9-volt battery. Today over 90 percent of households that are equipped with fire detectors use the ionization type smoke detectors.

Despite their low cost, relatively maintenance-free operation and wide acceptance by the buying public, the smoke detectors are not without problems and certainly far from being ideal. There are a number of significant drawbacks for the ionization smoke detectors to operate successfully as early warning fire detectors. To state it plainly, most people do not complain about them simply because there are no better alternatives.

One of the biggest problems with ionization smoke detectors is their frequent false-alarms. By the nature of its operational principle, any micron-size particulate matter other than the smoke from an actual fire can set off the alarm. Kitchen grease particles generated by a hot stove is one classic example. Over-zealous dusting of objects and/or furniture near the detector is another. Frequent false-alarms are not just a harmless nuisance; some people actually disarm their smoke detectors by temporarily removing the battery in order to escape from such annoying episodes. This latter situation could be outright dangerous especially when these people forget to rearm their smoke detectors.

Another significant drawback for the current ionization smoke detector is its relatively slow speed to alert people of a fire. There are several factors that contribute to this particular drawback. The first fact is the detector trigger threshold for smoke which directly affects its response time to the onset of a fire. No doubt a lower trigger threshold would mean a faster fire detector. However, it also means more frequent annoying false alarms for the user. The second factor is the particular placement of the detector with respect to the spot where fire breaks out. Unlike ordinary gases, smoke is actually a complex sooty molecular cluster that consists mostly of carbon. It is much heavier than air and thus diffuses much slower than the gases we encounter everyday. Therefore, if the detector happens to be at some distance from the location of the fire, it will be a while before enough smoke gets into the sampling chamber of the smoke detector to trigger the alarm. A third factor is the nature or type of fire itself. Although smoke usually accompanies fire, the amount produced can vary significantly depending upon the composition of the material that catches fire. For example oxygenated fuels such as ethyl alcohol and acetone give less smoke than the hydrocarbons from which they are derived. Thus, under free-burning conditions oxygenated fuels such as wood and polymethylmethacrylate give substantially less smoke than hydrocarbon polymers such as polyethylene and polystyrene. As a matter of fact a small number of pure fuels namely carbon monoxide, formaldehyde, metaldehyde, formic acid and methyl alcohol burn with non-luminous flames and do not produce smoke at all.

Yet another drawback of present-day ionization smoke detectors has to do with contaminating our environment. Ionization type smoke detectors use a radioactive matter ($Co^{60}$) as the source for alpha particles. Although one can argue that the amount of radioactive material currently found in each ionization smoke detector is very small (probably only tens of milligrams) the number of units in operation however easily runs into tens of millions every year. Thus, the continued usage of this type of smoke detector does pose a serious long-term liability of building up a large amount of unwanted nuclear wastes. Since the half life of $Co^{60}$ is well over 1,000 years, the potential danger should not be ignored.

Finally, there are a number of lesser issues one has to deal with when using these low-cost ionization smoke detectors. These include the trouble and cost of having to replace its battery once every year or run the risk of owning a unit that does not work because of lack of power. Also, the presently available ionization smoke detectors are rarely equipped with a visual alarm which is desirable for hearing-impaired persons.

Based upon the discussion presented above, it is clear that a rapid, reliable, low-cost, radioactive-free and maintenance-free fire detector would be a most welcome addition to the imperfect world of fire detectors In U.S. Pat. No. 4,738,266, issued Apr. 19, 1988, Thatcher describes an instrument for sensing a change in the carbon dioxide concentration in ambient air. The device uses an unmodulated broadband infrared source operated at a steady temperature and a single pass band filter. In contrast with the present invention, there is no provision in Thatcher's instrument for avoiding false alarms caused by a gradual build-up of particles of dust on the surfaces of the optical system or caused by gradual deterioration of the components. Clearly, these factors are significant for a fire detector, and the ability of the present invention to avoid confounding these factors with the carbon dioxide measurement shows the importance of the differences between the present invention and that of Thatcher.

In U.S. Pat. No. 4,648,396 issued Mar. 10, 1987, Raimer shows apparatus for monitoring the difference in carbon dioxide content between an individual's inspired and expired gas streams. The apparatus is similar to that described in the Thatcher patent, except that a feedback loop is used to maintain the level of radiation incident on the detector constant regardless of window clouding, temperature-induced component drift, etc. The derivative of the detected signal is checked to rule out noise as a source of error in the carbon dioxide measurement.

A number of other patents show one or more features in common with the present invention, but the patents in this class all make use of moving parts (typically rotating filter wheels) or other components which are deemed to be unsuitable for use in a fire detector. These patents include: U.S. Pat. No. 4,785,184 to Bien, et al.; U.S. Pat. No. 4,874,572 to Nelson, et al.; U.S. Pat. No. 4,587,427 to Talbot, et al.

SUMMARY OF THE INVENTION

A major purpose of the present invention is to provide a reliable and low-cost fire detector that is free from the use of radioactive material such as the alpha particle source found in present-day ionization smoke detectors. The present invention has no moving parts.

Another major purpose of the present invention is to introduce a totally new method of detecting early fires which is faster and false-alarm proof for responding to fire initiation without exceptions.

It has been known for a long time that as a process, fire can take many forms, all of which however involve chemical reaction between combustible species and oxygen from the air. In other words, fire initiation is necessarily an oxidation process since it invariably involves the consumption of oxygen at the beginning. The most effective way to detect fire initiation, therefore, is to look for and detect end products of the oxidation process. With the exception of a few very specialized chemical fires (i.e., fires involving chemicals other than the commonly encountered hydrocarbons) there are three elemental entities (carbon, oxygen and hydrogen) and three compounds (carbon dioxide, carbon monoxide and water vapor) that are invariably involved in the ensuing chemical reactions or combustion of a fire.

Of the three effluent gases that are generated at the onset of a fire, carbon dioxide is the best candidate for detection by a fire detector. This is because water vapor is a very difficult gas to measure since it tends to condense easily on every available surface causing its concentration to fluctuate wildly dependent upon the environment. Carbon monoxide, on the other hand, is invariably generated in a lesser quantity than carbon dioxide, especially at the beginning of a fire. It is only when the fire temperature gets to 600° C. or above that more of it is produced at the expense of carbon dioxide and carbon. Even then more carbon dioxide is produced than carbon monoxide according to numerous studies of fire atmospheres in the past. In addition to being generated abundantly right from the start of the fire, carbon dioxide is a very stable gas. Its concentration can easily be measured accurately using Non-Dispersive Infrared (NDIR) techniques that are very advanced at the present time. The average ambient $CO_2$ concentration level of $\sim$ 200 ppm ($\sim$ 0.02%) does not hinder the detection of additional fire-induced quantities as long as the carbon dioxide sensor is designed to have such a fine sensitivity.

Another very significant advantage of using a carbon dioxide detector rather than a smoke detector for fire initiation detection is the relative mobility of these diverse species. Smoke generation is a direct result of incomplete combustion leading to the formation of complex flammable tarry substances that, upon thermal decomposition, develop into sooty molecular clusters that consist mostly of carbon. Consequently, smoke is much heavier than carbon dioxide and therefore tends to diffuse slower in the atmosphere. Therefore, if a smoke detector and a carbon dioxide detector are located side by side some distance from a fire, the carbon dioxide detector will give the earlier alarm, primarily because of the greater mobility of the carbon dioxide gas.

Thus, a carbon dioxide detector would have definite performance advantages over the conventional smoke detector; but until the present invention, it was considered impossible to build a carbon dioxide detector that would be competitive with the smoke detector in terms of cost, sensitivity and reliability. The discussion below will demonstrate that the carbon dioxide detector of the present invention is, in fact, competitive in terms of cost, sensitivity and reliability, and superior in early warning time and freedom from false alarms.

In accordance with the present invention, radiation from a quasi-blackbody source that is pulsed electrically is conducted through a gas sample chamber to a detector that is equipped with a single pass band filter whose pass band is located at a strong absorption band of carbon dioxide. In the preferred embodiment the absorption band at 4.26 microns is used.

The detector generates an electrical signal related to the intensity of the radiation falling on it. This signal decreases as the concentration of carbon dioxide in the sample chamber increases as the fire develops. An electronic circuit responsive to this signal produces signals representative of the concentration of the carbon dioxide and representative of the rate of change of the concentration. These signals are compared with preset threshold levels and an alarm is generated in accordance with a built-in rule.

In the rapid fire detector of the first companion patent application referred to above, the sample chamber communicated directly with the ambient air. This was considered necessary to permit rapid diffusion of carbon dioxide into the sample chamber. Unfortunately, it also created the possibility that particles of smoke, dust, water or oil could also enter the sample chamber, depositing themselves on the optical components and thereby decreasing the signal generated by the detector. Unless some precaution were taken, the system would interpret this decrease in signal as being caused by absorption and would produce a false alarm.

To avoid this possibility, the rapid fire detector of the first companion patent application employed a dual wavelength technique, using (in addition to the 4.26 micron absorption band) radiation of a second wavelength (for example 2.20 microns) at which none of the gases present in the air in the sample chamber absorbs. Any decrease in the signal in this second reference channel could not be attributed to absorption, and would therefore have to be attributed to some factor common to both channels, such as dust on the optical components. This reasoning was implemented by calculating the ratio of the signal in the 4.26 micron channel to the signal in the 2.20 micron channel; i.e., by normalizing the signal in the 4.26 micron channel.

This approach is certainly valid, but overly conservative; its principal disadvantage being the cost of the dual-pass band filter and of the microprocessor used to process the signals.

The present invention permits the substitution of a single pass band filter and, optionally, the use of simpler signal processing circuitry.

The present invention involves imposing a particle filter in the path leading to the sample chamber from the air surrounding the fire detector, so that all particles are filtered out before they reach the sample chamber where the optical components are. Thus, in the present invention the emphasis is on keeping particles of smoke, dust, water and oil out of the sample chamber, rather than on compensating electronically for their presence.

The undesirable particles range in size from about 5.0 microns down to as little as 0.01 micron. A simple mesh would not be nearly fine enough, and a high quality filter would probably cost too much. This dilemma was solved by the present inventor who remembered the well-established fact that a sheet of silicone rubber is remarkably permeable by carbon dioxide gas. This effect is used to advantage in heart-lung machines in the medical field; it was first described by K. Kammermeyer in an article titled "Silicone Rubber as a Selective Barrier: Gas and Vapor Transfer", and published in the Ind. Engr. Chem. Vol. 49, p. 1685-1686 (1957).

The application of this esoteric knowledge to the design of a fire detector was the key that opened up the possibility of a very inexpensive fire detector capable of giving an earlier warning than the smoke detectors currently used in millions of homes.

The silicone rubber membrane keeps out the objectionable particles of smoke, dust, water and oil but readily passes molecules of carbon dioxide gas. The need for a reference channel ceases to exist, and the costly dual pass band filter can be replaced with a less expensive single pass band filter. The electronics can then be simplified, yielding a further cost reduction.

The result (the present invention) is a fire detector that is very competitive in cost with conventional smoke detectors, but uses no radioactive material. It gives an earlier warning with fewer false alarms, and has the potential for saving thousands of lives and millions of dollars in property each year.

A more detailed description of this remarkable instrument will be given below with the aid of the accompanying drawings which are intended to illustrate two possible embodiments of the invention. Clearly other embodiments are possible, and they also are embraced within the scope of the invention.

DETAILED DESCRIPTION OF THE PREFERRED EMBODIMENT

Figure 2:
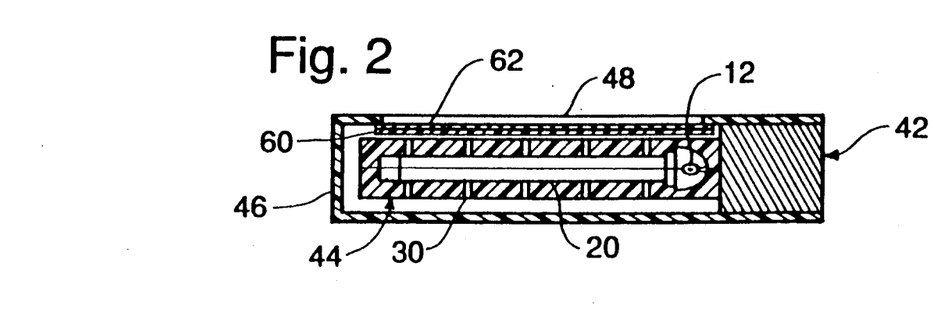
FIG. 2 is a side elevational cross sectional view of the embodiment shown in FIG. 1.
Figure 4:
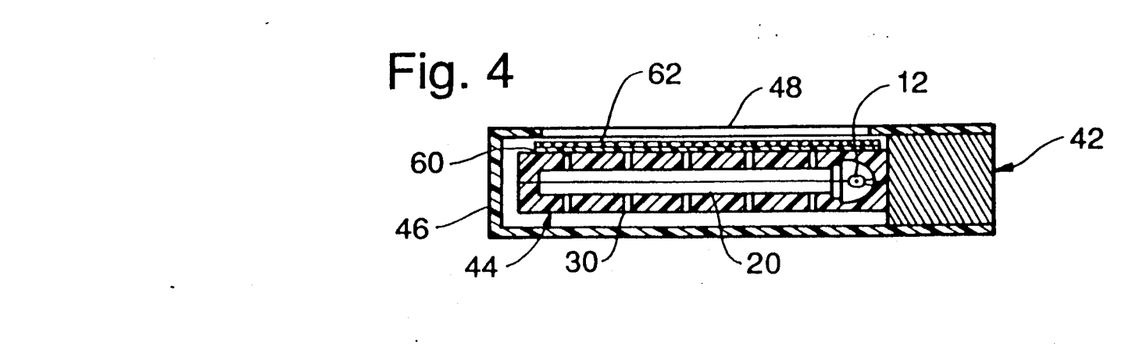
FIG. 4 is a side elevational cross sectional view of the embodiment shown in FIG. 3; and, FIG. 5 is a block diagram showing the electronic circuitry, which is common to both of the preferred embodiments.

From a mechanical standpoint, the three main portions of the fire detector are the electronic compartment 42, the sample chamber 44, which is attached to the electronic compartment 42, and the housing 46 which, as seen in FIGS. 2 and 4, encloses the sample chamber 44, and which is attached to the electronic compartment 42.

Figure 5:
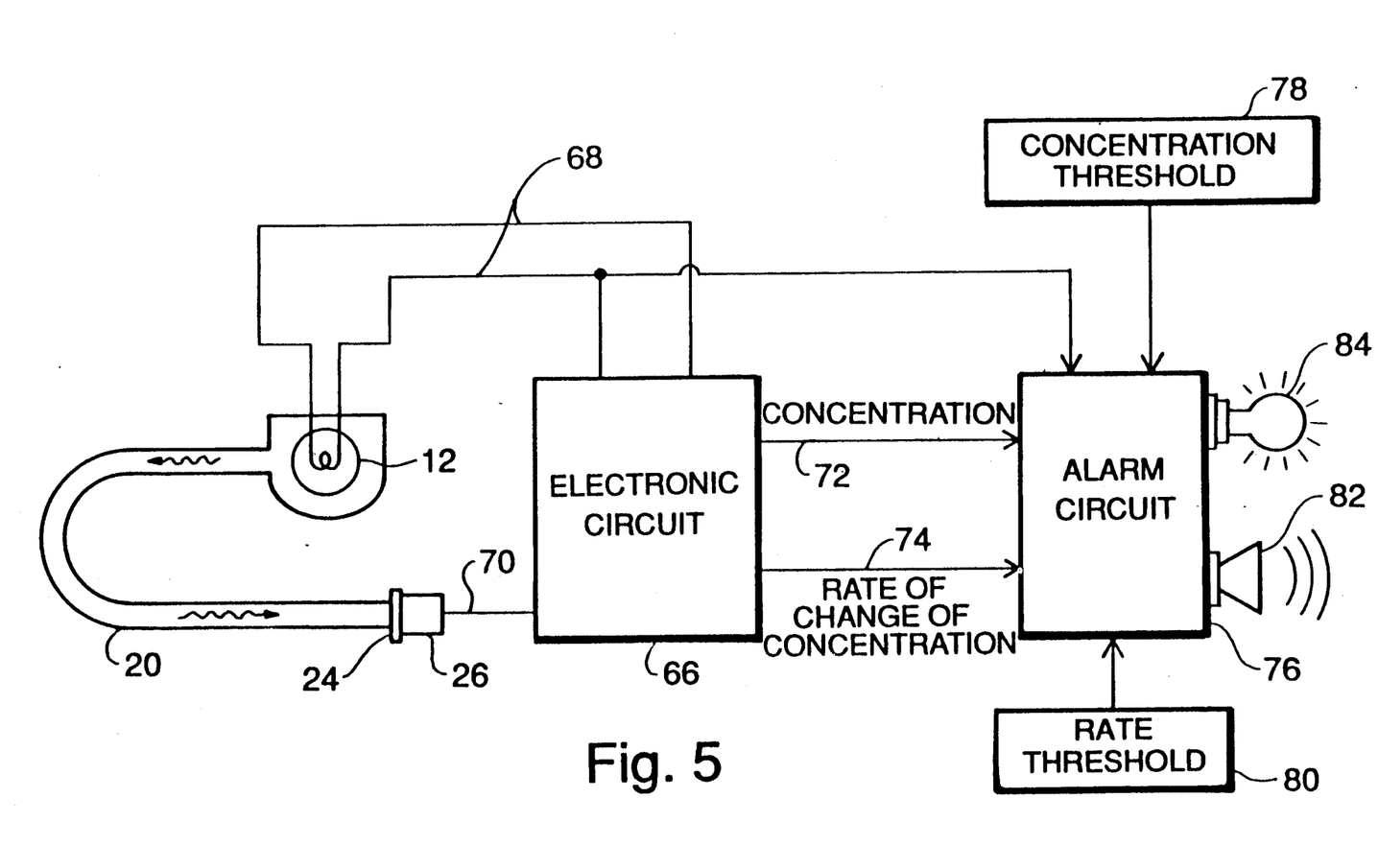

The electronic compartment 42 contains the circuits shown in FIG. 5, including the electronic circuit and the alarm circuit as well as an audible alarm, a visible alarm, and, in one variation, batteries to power the device.

As described more completely in a copending patent application of the present inventor, filed on the same date as the present application and titled "Gas Sample Chamber" the sample chamber 44 consists of two identical halves 50, 52, in a preferred embodiment. The halves include portions that define an extended passage 20 that conducts radiation emitted by the source 12 on an indirect extended path that ultimately leads to the filter 24 and the detector 26. A number of passages, of which the passage 30 is typical connect the space within the extended passage 20 with the space immediately surrounding the sample chamber 44. The passages 30 permit carbon dioxide gas to diffuse into the extended passage 20 where it absorbs some of the radiation, thereby decreasing the amount of radiation reaching the detector 26. The amount of absorption is related to the concentration of the carbon dioxide in the extended passage 20.

In the preferred embodiment, the source 12 is a miniature conductor that is heated by an electrical current and that emits a spectrum of radiation approximating the spectrum of a blackbody source. In the preferred embodiment, the source 12 is turned off and on at 0.5 second intervals, that is, it is modulated at a frequency of 1.0 Hz.

In a variation of the present invention, the source 12 is a laser diode.

In accordance with the preferred embodiment, the source 12 emits radiation in the 4.26 micron absorption band of carbon dioxide. The filter 24 serves to limit the radiation reaching the detector 26 to the same wavelength band. If the source 12 is a semiconductor laser, the filter 24 is not used.

The housing 46 is a hollow box-like part that may be molded of plastic or that may be formed of sheetmetal.

The housing 46 includes apertures of which the aperture 48 is typical.

Figure 1:
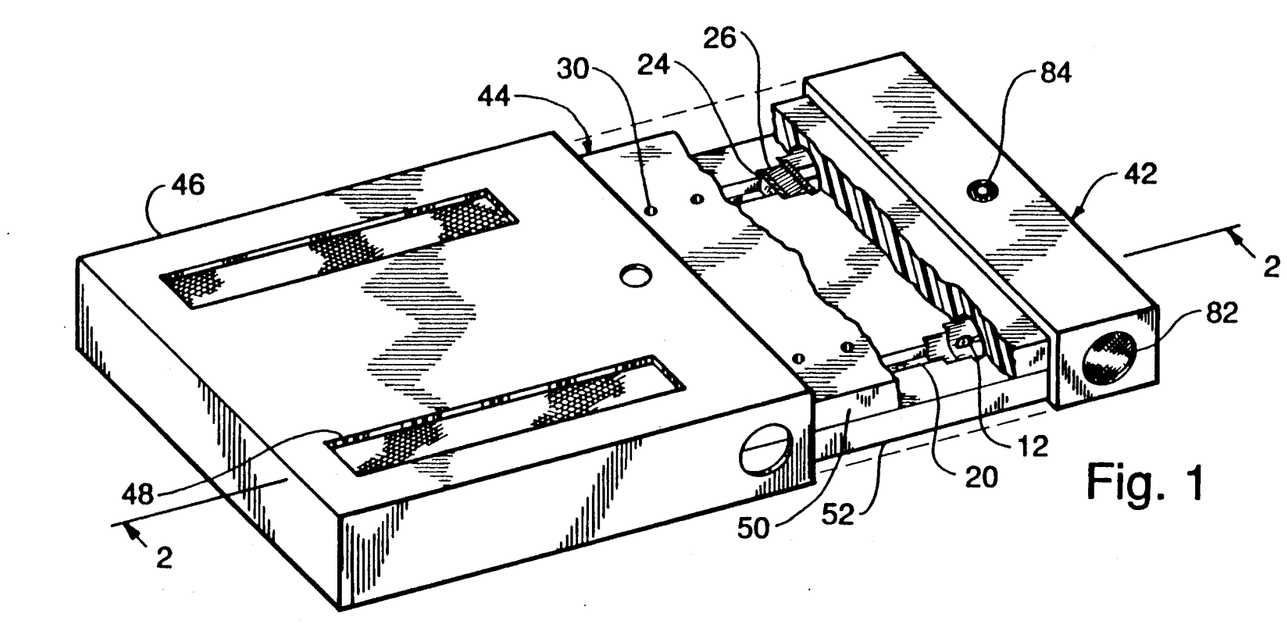
FIG. 1 is an exploded perspective view partly cut away and showing a first preferred embodiment of the fire detector of the present invention.

In accordance with the present invention, in the embodiment of FIGS. 1 and 2, the aperture 48 is covered by a matrix 62 which supports a membrane 60. The membrane 60 is composed of silicon rubber, and the matrix consists of a thin layer of a very permeable fabric such as glass fiber or the material of ladies nylon hosiery. Although the permeability of silicon rubber to carbon dioxide gas is firmly established, the present invention encompasses other membranes that are permeable to carbon dioxide while remaining impermeable to particles of smoke, dust, water, and oil. For example, air-cleaning filters are readily available for filtering out particles as small as 0.01 microns while permitting air to pass through.

Figure 3:
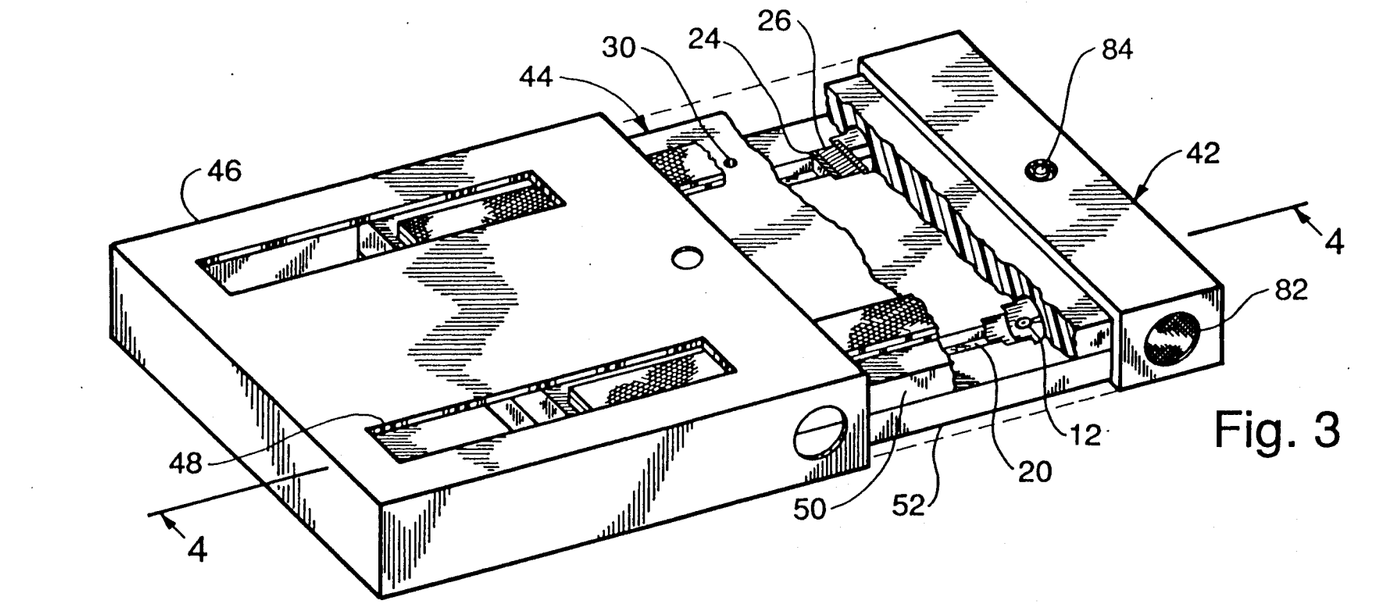
FIG. 3 is an exploded perspective view partly cut away and showing a second preferred embodiment of the fire detector of the present invention.

FIGS. 3 and 4 show a second preferred embodiment which differs from the first preferred embodiment only in the location of the permeable layer 60. In this second preferred embodiment, the permeable layer 60 is attached to the sample chamber 44 rather than to the housing 46. The permeable layer spans the passage 30 of the sample chamber 44. Since the passages 30 are the only path by which access is gained to the extended passage 20, it follows that the unwanted particles of smoke, dust, water and oil will be kept out of the extended passage 20 but carbon dioxide is able to reach the extended passage 20 by difusion through the permeable layer and through the passages 30. In this second embodiment, the housing 46 is provided with apertures 48 to permit ambient air to communicate with the space between the housing and the sample chamber.

FIG. 5 shows the components that are located in the electronic compartment 42.

The electronic circuit 66 produces timed pulses of current on the lines 68 to drive the source 12. The source emits radiation that travels through the extended passage through the filter 24 and that impinges on the detector 26. The detector 26 produces an electrical signal on the line 70 representative of the intensity of the radiation falling upon it. The signal thus produced on the line 60 is applied to the electronic circuit 66.

In the preferred embodiment, AC circuitry is used, and consistent with that approach, the source 12 is pulsed at a rate on the order of 1.0 Hz.

In other embodiments, DC circuitry is used, and the source 12 is operated continuously.

When there is no fire, the constant magnitude of the pulses of current applied to the source 12 results in a series of pulses on the line 70 of constant magnitude. Background radiation falling on the detector 26 is steady, and produces a DC component on the line 70 which is eliminated by the AC circuitry. If a fire develops, the concentration of carbon dioxide in the extended passage increases, and because the carbon dioxide absorbs some of the radiation emitted by the source 12, the amplitude of the signal on the line 70 decreases. The amount of decrease resulting from a particular level of concentration of carbon dioxide gas can be established by calibrating the instrument under controlled conditions. Thus, the concentration of carbon dioxide is related to the decrease in the amplitude of the signal on the line 70. The electronic circuit 66 produces a signal on the line 72 that is representative of the concentration of carbon dioxide. The electronic circuit also produces a signal on the line 74 that is related to the rate of change of the concentration of carbon dioxide. The signals on the lines 72 and 74 are applied to the alarm circuit 76. That circuit also receives a threshold level of concentration from the potentiometer 78 and a threshold level for the rate of change of concentration from the potentiometer 80. The alarm circuit 76 compares the concentration of carbon dioxide with the threshold level set on the potentiometer 78 and compares the rate of change of the concentration as represented by the signal on the line 74 with the rate threshold that has been preset on the potentiometer 80.

Several options are available at this point. In the preferred embodiment, false alarms are minimized by requiring that both the concentration and its rate of change must exceed their respective threshold levels before the alarm will be activated. In another embodiment, the alarm is activated if either the concentration or the rate of change of the concentration exceeds its respective threshold. This mode is necessarily faster, but is likely to produce a greater number of false alarms. In yet another embodiment, a compromise between response time and false alarms is achieved by forming a linear combination of the concentration and its rate of change, and by activating the alarm when the linear combination exceeds some threshold.

In the preferred embodiment, when the alarm is activated, electricity is applied to both the audible alarm generator 82 and the visible alarm generator 84.

Calibration of the fire detector can be accomplished by placing it in a special atmosphere that includes a concentration of carbon dioxide that is considered to be a significant increase, i.e., of the magnitude that might be expected when a fire starts, and by adjusting the potentiometer 78 to gradually lower the threshold level until the alarm is sounded.

Likewise, the calibration for the rate of change of the concentration could, in theory, be accomplished by electronically simulating an increasing concentration of carbon dioxide, permitting the electronic circuits 66 to generate the rate signal on the line 74, and adjusting the potentiometer 80 to gradually lower the rate threshold until the alarm is sounded.

These techniques for calibrating the fire detector take advantage of the fact that the operation of the fire detector does not require an absolute measurement of the concentration or its rate of change, but only signals that are related to these quantities in a consistent manner.

Thus, there has been described an extremely simple and inexpensive fire detector that provides earlier warning than the commonly used smoke detectors, because its operation is related, not to smoke, but to the build-up of carbon dioxide that accompanies a fire.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. A fire detector that senses a build-up in the ambient air of carbon dioxide that is produced by a fire, said fire detector having no moving parts and comprising in combination:
   a source capable of emitting radiation having a wavelength coinciding with an absorption band of carbon dioxide;
   a detector generating an electrical signal in response to the radiation falling on it;
   a sample chamber containing air and including a passage communicating with the ambient air, said sample chamber including means defining a path for emitted radiation through said sample chamber, said source located at one end of the path and said detector located at the other end of the path;
   said sample chamber further including membrane means permeable to carbon dioxide gas, spanning the passage of said sample chamber and keeping smoke, dust, oil and water out of said sample chamber while freely permitting carbon dioxide in the ambient air to pass into the sample chamber;
   electronic means electrically connected to said detector and responsive to an electrical signal generated by it to produce a signal representative of the rate of change of the concentration of carbon dioxide in said sample chamber, and
   alarm means connected to said electronic means and responsive to an increase in the signal representative of the rate of change of the concentration of carbon dioxide generated by the fire to produce an alarm in accordance with preset criterion.

2. The fire detector of claim 1 wherein said preset criterion is that the signal representative of the rate of change of the concentration exceeds a preset threshold level.

3. A fire detector that sense a build-up in the ambient air of carbon dioxide that is produced by a fire, said fire detector having no moving parts and comprising in combination:
   a source capable of emitting radiation having a wavelength coinciding with an absorption band of carbon dioxide;
   a detector generating an electrical signal in response to the radiation falling on it;
   a sample chamber containing air and including a passage communicating with the ambient air, said sample chamber including means defining a path for the emitted radiation through said sample chamber, said source located at one end of the path and said detector located at the other end of the path;
   said sample chamber further including membrane means permeable to carbon dioxide gas, spanning the passage of said sample chamber and keeping smoke, dust, oil and water out of said sample chamber while freely permitting carbon dioxide in the ambient air to pass into the sample chamber;
   electric means electrically connected to said detector and responsive to an electrical signal generated by it to produce a signal representative of the concentration of carbon dioxide in said sample chamber, and
   alarm means connected to said electronic means and responsive to an increase in the signal representative of the concentration of carbon dioxide produced by the fire to produce an alarm in accordance with preset criterion.

4. The fire detector of claim 3 wherein said preset criterion is that the signal representative of the concentration of carbon dioxide exceeds a preset threshold level.

5. Apparatus for use in a fire detector that senses a build-up in the ambient air of carbon dioxide that is produced by a fire, said apparatus having no moving parts and comprising in combination:
   a source capable of emitting radiation having a wavelength coinciding with an absorption band of carbon dioxide;
   a detector generating an electrical signal in response to the radiation falling on it;
   a sample chamber containing air and including a passage communicating with the ambient air, said sample chamber including means defining a path for the emitted radiation through said sample chamber, said source located at one end of the path and said detector located at the other end of the path;
   said sample chamber further including membrane means permeable to carbon dioxide gas, spanning the passage of said sample chamber and keeping smoke, dust, oil and water out of said sample chamber while freely permitting carbon dioxide in the ambient air to pass into the sample chamber;
   electronic means electrically connected to said detector and responsive to an electrical signal generated by it to produce a first signal representative of an increase in the concentration of carbon dioxide produced by the fire in said sample chamber and to produce a second signal representative of an increase in the rate of change of the concentration of carbon dioxide produced by the fire in said sample chamber.

6. The apparatus of claim 5 further comprising:
   alarm means connected to said electronic means and responsive to said first signal and to said second signal to produce an alarm signal only when both said first signal and said second signal exceed their respective preset thresholds.

7. The apparatus of claim 5 further comprising:
   alarm means connected to said electronic means and responsive to said first signal and to said second signal to produce an alarm signal when either said first signal or said second signal exceeds its preset threshold.

8. The apparatus of claim 5 further comprising:
   alarm means connected to said electronic means and responsive to said first signal and to said second signal to produce a combined signal that is a linear combination of said first signal and said second signal and to produce an alarm signal when the combined signal exceeds a preset threshold.

9. A fire detector that sense build-up in the ambient air of carbon dioxide that is produced by a fire, said fire detector having no moving parts and comprising in combination:
   a source capable of emitting radiation having a wavelength coinciding with an absorption band of carbon dioxide:
   a detector generating an electrical signal in response to the radiation falling on it;
   a sample chamber containing air and including a passage communicating with the air surround said sample chamber, said sample chamber including means defining a path for the emitted radiation through said sample chamber, said source located at one end of the path and said detector located at the other end of the path;

a housing including an aperture and surround said sample chamber so that the only way the sample chamber can communicate with the air surrounding the housing is through the aperture;

membrane means permeable to carbon dioxide gas, spanning the aperture of said housing and keeping smoke, dust, oil and water out of the space within the housing while freely permitting carbon dioxide to pass, via the aperture and the passage into sample chamber;

electronic means electrically connected to said detector and responsive to an electrical signal generated by it to produce a signal representative of the rate of change of the concentration of carbon dioxide in said sample chamber, and alarm means connected to said electronic means and responsive to an increase in the signal representative of the rate of change of the concentration of carbon dioxide produced by the fire to produce an alarm in accordance with preset criterion.

10. The fire detector of claim 9 wherein said preset criterion is that the signal representative of the rate of change of the concentration exceeds a preset threshold level.

11. A fire detector that senses a build-up in the ambient air of carbon dioxide that is produced by a fire, said fire detector having no moving parts and comprising in combination:

a source capable of emitting radiation having a wavelength coinciding with an absorption band of carbon dioxide;

a detector generating an electrical signal in response to the radiation falling on it;

a sample chamber containing air and including a passage communicating with the air surrounding said sample chamber, said sample chamber including means defining a path for the emitted radiation through said sample chamber, said source located at one end of the path and said detector located at the other end of the path;

a housing including an aperture and surrounding said sample chamber so that the only way the sample chamber can communicate with the air surrounding the housing is through the aperture;

membrane means permeable to carbon dioxide gas, spanning the aperture of said housing and keeping smoke, dust, oil and water out of the space within the housing while freely permitting carbon dioxide to pass, via the aperture and the passage into sample chamber;

electronic means electrically connected to said detector and responsive to an electrical signal generated by it to produce a signal representative of the concentration of carbon dioxide in said sample chamber, and alarm means connected to said electronic means and responsive to an increase in the signal representative of the concentration of carbon dioxide produced by the fire to produce an alarm in accordance with preset criterion.

12. The fire detector of claim 11 wherein said preset criterion is that the signal representative of the concentration of carbon dioxide exceeds a preset threshold level.

13. Apparatus for use in a fire detector that sense a build-up in the ambient air of carbon dioxide that is produced by a fire, said apparatus having no moving parts and comprising in combination:

a source capable of emitting radiation having a wavelength coinciding with an absorption band of carbon dioxide;

a detector generating an electrical signal in response to the radiation falling on it;

a sample chamber containing air and including a passage communicating with the air surrounding said sample chamber, said sample chamber including means defining a path for the emitted radiation through said sample chamber, said source located at one end of the path and said detector located at the other end of the path;

a housing including an aperture and surrounding said sample chamber so that the only way the sample chamber can communicate with the air surrounding the housing is through the aperture;

membrane means permeable to carbon dioxide gas, spanning the aperture of said housing and keeping smoke, dust, oil and water out of the space within the housing while freely permitting carbon dioxide to pass, via the aperture and the passage into sample chamber;

electronic means electrically connected to said detector and responsive to an electrical signal generated by it to produce a first signal representative of an increase in the concentration of carbon dioxide produced by the fire in said sample chamber and to produce a second signal representative of an increase in the rate of change of the concentration of carbon dioxide produced by the fire in said sample chamber.

14. The apparatus of claim 13 further comprising:
alarm means connected to said electronic means and responsive to said first signal and to said second signal to produce an alarm signal only when both said first signal and said second signal exceed their respective preset thresholds.

15. The apparatus of claim 13 further comprising:
alarm means connected to said electronic means and responsive to said first signal and to said second signal to produce an alarm signal when either said first signal or said second signal exceeds its preset threshold.

16. The apparatus of claim 13 further comprising:
alarm means connected to said electronic means and responsive to said first signal and to said second signal to produce a combined signal that is a linear combination of said first signal and said second signal and to produce an alarm signal when the combined signal exceeds a preset threshold.

17. The fire detector of claims 1, 3, 9, or 11 wherein said membrane means comprise a film composed of silicone rubber.

18. The fire detector of claims 1, 3, 9, or 11 wherein said membrane means further comprise a film composed of silicon rubber and a sheet of a matrix to which said film is attached for reinforcement.

19. The fire detector of claims 1, 3, 9, or 11 wherein said source emits radiation in the 4.26 micron absorption band of carbon dioxide.

20. The fire detector of claims 1, 3, 9, or 11 further comprising in combination a narrow bandpass filter interposed in the path between said source and said detector, and transmitting radiation in the 4.26 micron absorption band of carbon dioxide.

21. The apparatus of claims 5 or 13 wherein said membrane means further comprise a film composed of silicon rubber.

22. The apparatus of claims 5 or 13 wherein said membrane means further comprise a film composed of silicon rubber and a sheet of a matrix to which said film is attached for reinforcement.

23. The apparatus of claims 5 or 13 wherein said source emits radiation in the 4.26 micron absorption band of carbon dioxide.

24. The apparatus of claims 5 or 13 further comprising in combination a narrow bandpass filter interposed in the path between said source and said detector, and transmitting radiation in the 4.26 micron absorption band of carbon dioxide.

* * * * *